United States Patent [19]
Akiba et al.

[11] Patent Number: 5,894,369
[45] Date of Patent: Apr. 13, 1999

[54] LENS DEVICE WITH ANTI-FOGGING

[75] Inventors: Harou Akiba; Naotake Mitsumori; Joji Watanabe; Yuichi Torii, all of Omiya, Japan

[73] Assignee: Fuji Photo Optical Co., Ltd., Omiya, Japan

[21] Appl. No.: 08/967,659

[22] Filed: Nov. 10, 1997

[30] Foreign Application Priority Data

| Nov. 15, 1996 | [JP] | Japan | 8-318600 |
| Nov. 22, 1996 | [JP] | Japan | 8-325860 |
| Dec. 10, 1996 | [JP] | Japan | 8-344489 |
| Feb. 26, 1997 | [JP] | Japan | 9-057092 |

[51] Int. Cl.$^6$ .................. G02B 7/02; G02B 11/04
[52] U.S. Cl. .................. 359/820; 359/512; 600/109; 600/110; 600/129; 600/130; 348/65
[58] Field of Search .................. 359/819, 820, 359/512; 600/122, 130, 131, 133, 109, 110, 129; 348/65

[56] References Cited

U.S. PATENT DOCUMENTS

| 4,525,745 | 6/1985 | Ghaem-Maghami et al. | 359/820 |
| 4,779,613 | 10/1988 | Hashiguchi et al. | 359/512 |
| 4,832,003 | 5/1989 | Yabe | 600/109 |
| 4,867,137 | 9/1989 | Takahashi | 600/109 |
| 4,971,035 | 11/1990 | Ito | 600/129 |
| 4,993,405 | 2/1991 | Takamura et al. | 600/110 |
| 5,188,094 | 2/1993 | Adair | 600/122 |
| 5,557,474 | 9/1996 | McCrary | 359/820 |

*Primary Examiner*—Loha Ben
*Attorney, Agent, or Firm*—Oblon, Spivak, McClelland, Maier & Neustadt, P.C.

[57] ABSTRACT

An anti-fogging lens device, having a plural number of optical glass lens elements mounted within a lens barrel, including a first lens element located in a foremost position on the side of a subject and a second lens element located behind and at a space from the first lens element. A spacer ring is fitted in the lens barrel to set apart the first and second lens elements by a gap space of a predetermined width. The spacer ring is formed of a material having higher thermal conductivity than the lens elements and, on the inner peripheral side thereof, provided with a moisture depositing surface which is formed in a non-flat shape to increase its surface area. The lens barrel is fitted in a cylindrical member, and a seal pocket, to be packed with a seal material, is formed between the lens barrel and the cylindrical member to stop clearances between these two members with a secure hermetical seal.

12 Claims, 8 Drawing Sheets

LENS DEVICE WITH ANTI-FOGGING

FIELD OF THE ART

This invention relates to a lens device suitable for use as an objective lens on an optical imaging system of endoscopic instrument, and more particularly to a lens device with anti-fogging functions.

PRIOR ART

Extended out on the front side of a manipulating head grip of endoscope is a rod-like insertion instrument for introduction into a body cavity. The insertion instrument or rod contains components of illumination and observation systems which are necessary for endoscopic observations or examinations. Led out on the rear side of the manipulating head grip is a so-called universal cable which contains a light guide in the form of a bundle of fiber optics to send forward illumination light from a light source. The universal cable is usually disconnectibly connected to a connection terminal of a light source with a source lamp. The fore light emitting end of the light guide is coextensively passed through the endoscopic insertion rod down to a light projecting window of the illumination system, which is provided at the fore distal end of the endoscopic insertion rod. An illumination lens is fitted in the light projecting window for the purpose of dispersing illumination light which is emitted from the light guide. On the other hand, the observation system serves to pick up images of intracavitary portions which are lighted up by the illumination system.

By the type of image pickup system, the endoscopes can be classified into two types. The first one is an optical endoscope which is arranged to transfer optical images through an optical image guide to an eyepiece which is provided on or in the vicinity of the manipulating head grip, so that an operator can view the images of intracavitary portions through the eyepiece. The second one is an electronic endoscope which is provided with a photoelectric image sensor device like CCD thereby to convert images of intracavitary portions under observation into electric signals, which are then processed by a signal processor to display video images of the intracavitary portions on a viewing screen. In any case, components for the endoscopic observation system, including an objective lens, are built into a fore end portion of the insertion rod. Normally, the objective lens is composed of a plural number of lens elements which are mounted in a lens barrel. In the case of an optical endoscope, an input end of a light guide is located at the focus of the objective lens, and, in the case of an electronic endoscope, a photoelectric image sensor is located in that position. The respective lens elements of the objective lens are mounted in a lens barrel which is built into a rigid tip end section of the endoscopic insertion rod.

For the purpose of securing a wide view field, a wide angle lens system is usually employed as an objective lens, and, of a plural number of objective lens elements, the first lens element which is located in a foremost position on the side of subject is constituted by a concave lens. From the standpoint of reducing complicate irregularities in contour at the distal end of the endoscopic insertion rod, the first lens is preferred to be in the form of a plano-concave lens which is fitted in a lens barrel with its flat surface on the outer side, that is, on the side of the subject. Consequently, the first lens element is normally required to have a concave surface of extremely large curvature on the inner side thereof. Besides, it is necessary to provide an air gap of a predetermined width between the first lens and a second lens element which is located on the rear side of the first lens element.

While the endoscopic insertion rod is retained within a body cavity for an examination, the exterior surfaces of the first lens, which is exposed on the front side of the instrument, are often smudged by deposition of body fluids or other contaminants to such a degree as to cause considerable blurring to the images of intracavitary portions under observation. Therefore, it is usually the case that a lens surface washer is provided on the endoscopic insertion rod thereby to wash away deposited contaminant with a cleaning fluid. More specifically, normally deposited contaminants are washed away with a washing liquid which is spurted out from a nozzle which is provided on a lens surface washer, while residues of the washing liquid are removed from the lens surface by blasting compressed air thereon. Within a body cavity, the distal end portions of the endoscopic insertion rod, including the first lens, are warmed up to a temperature level which is almost same as the body temperature of the patient, and, in the case of an electronic endoscope which contains a heat-generating element like a solid-state image sensor, the first lens could reach a higher temperature level. Nevertheless, according to the general procedure, the washing liquid is supplied to the first lens of the objective lens assembly in an unheated state, that is to say, at the ambient temperature. Consequently, the first lens is quickly cooled off to a colder temperature as soon as the washing liquid is sprinkled on its surfaces.

When the first lens is quickly cooled off in this manner, fogging or moisture condensation occurs to the inner concave surface of the first lens element should moisture exist in the air gap between the first and second lenses. Besides, because of the large curvature of the inner concave surface, the first lens undergoes temperature drops most conspicuously in its thinner center portions or in the vicinity of its center portions. It follows that fogging or moisture condensation takes place concentratedly in center portions of the inner concave surface of the first lens, abruptly degrading the quality of images to an extremely obscured state because most of image-forming light rays are collected in center portions of the concave surface of the first lens.

In this regard, in order to prevent fogging or moisture condensation on the inner surface of the first lens, it has been known in the art to use a lens barrel having moisture-free dry air sealed in air spaces between the lens elements which are fitted in the barrel. Although the lens elements at the opposite ends of the lens barrel are mounted in a hermetically sealed state to retain dry air in the barrel, it is extremely difficult to maintain the dryness over a long period of time since dry air is gradually replaced by moistened air. Accordingly, the anti-fogging function which resorts to dry air has limits in time, suffering from deteriorations in anti-fogging effects upon lapse of a certain period of time.

SUMMARY OF THE INVENTION

In view of the situations as discussed above, it is an object of the present invention to provide a lens device with anti-fogging functions, which can maintain the anti-fogging functions over a long period of time.

It is another object of the present invention to provide a lens device which can prevent fogging or moisture condensation within a lens barrel, particularly in center areas of an inner concave surface of a first lens element located in a foremost position on the lens barrel.

It is still another object of the present invention to provide a lens device which is arranged to let moisture, if any, condense preferentially in those areas outside an effective diameter of a first lens element located in a foremost position on a lens barrel.

In accordance with the present invention, the above-stated objective are achieved by the provision of a lens device having a plural number of optical lens elements mounted in a cylindrical lens barrel, including a first lens element located in a foremost position on the side of a subject and a second lens element located behind and at a gap space from the first lens element, the lens device including a spacer ring fitted in the lens barrel to hold the first and second lens elements in a predetermined spaced relation, the spacer ring being formed of a material having higher thermal conductivity than the lens elements and provided with a moisture depositing surface of non-flat shape to increase the surface area thereof.

For increasing the surface area of the moisture depositing surface on the inner periphery of the spacer ring, it may be formed in an arcuately concave shape in cross section or formed with a plural number of tapped grooves. The lens device is particularly suitable for use on an endoscope by mounting the lens barrel as an objective lens of an optical imaging system on a distal end portion of an endoscopic insertion rod. The fore end face of the lens barrel is exposed to the outside at the distal end of the endoscopic insertion rod, and, whenever exterior surfaces of the insertion rod are cooled off, heat is efficiently conducted to the spacer ring from the fore end face of the lens barrel to let moisture condense preferentially on the moisture depositing surface on the inner periphery of the spacer ring if any.

According to another feature of the present invention, a seal pocket is provided between the lens barrel and prism frame. The seal pocket is packed with a seal material to stop clearances between the lens barrel and prism frame with a securer hermetical seal.

BRIEF DESCRIPTION OF THE DRAWINGS

The above and other objects, features and advantages of the invention will become apparent from the following particular description, taken in conjunction with the accompanying drawings which show by way of example preferred embodiments of the invention and in which.

DESCRIPTION OF PREFERRED EMBODIMENTS

Hereafter, the invention is described more particularly by way of its preferred embodiments with reference to the accompanying drawings. In the following description, the lens device according to the invention is applied as an objective lens of an endoscopic image pickup system. Needless to say, the lens device of the present invention can find other applications where anti-fogging functions are required.

Figure 1:
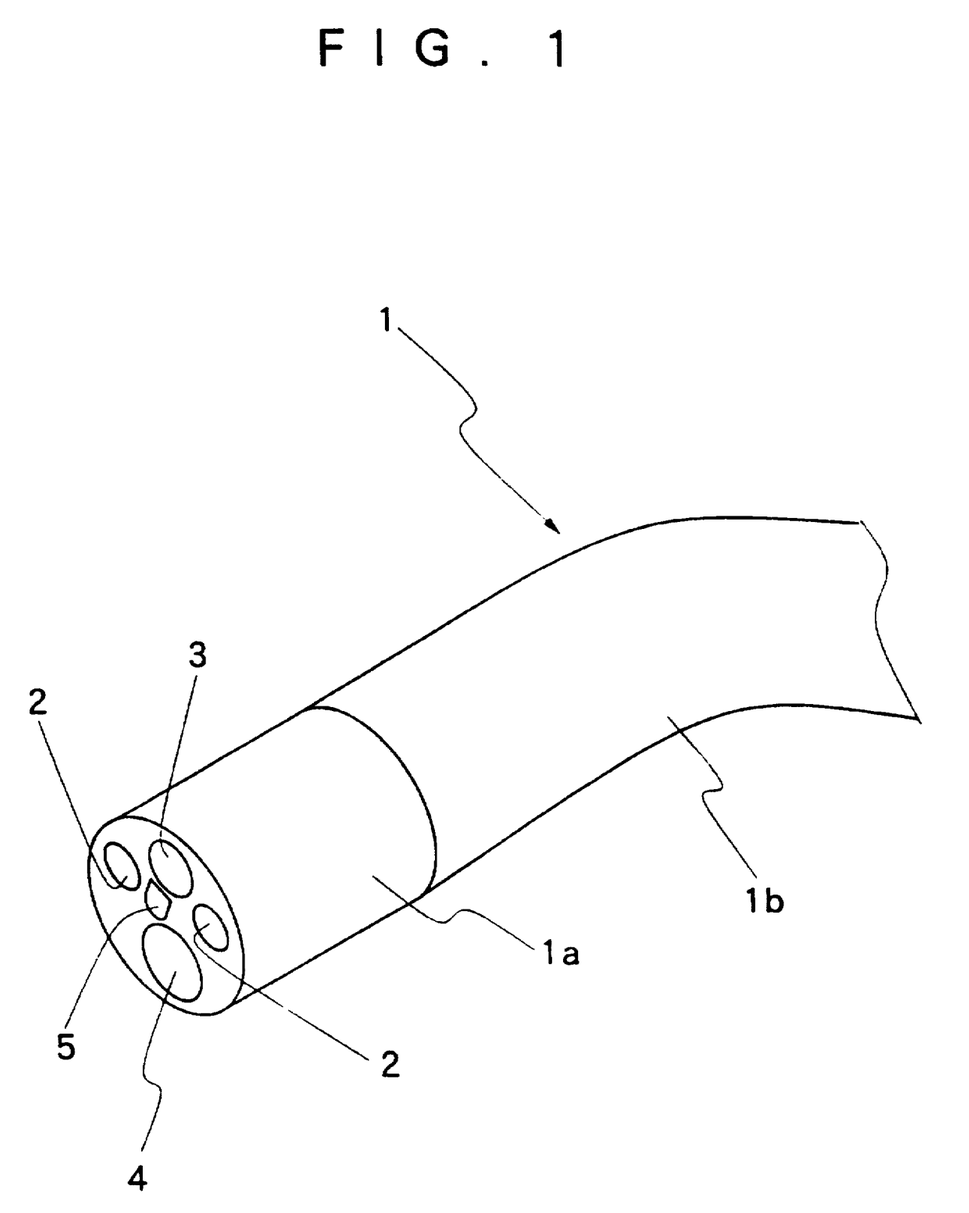
FIG. 1 is a schematic outer view of a fore end portion of an endoscopic insertion rod.

Referring first to FIG. 1, there is shown a fore end portion of an endoscopic insertion rod. In this figure, indicated at 1 is the insertion rod of an endoscope, which is provided a rigid tip end section 1a at its distal end. The tip end section 1a is connected to the distal end of the insertion rod 1 through an angle section 1b of a predetermined axial length, which can be flexibly bent into arbitrary directions and which is, although not shown in the drawing, connected to a main flexible body of the insertion rod 1. Provided on an end face portion (or on a lateral side) of the tip end section 1a are illumination and observation windows 2 and 3 of illumination and observation systems. Further, opened in the vicinity of these illumination and observation windows 2 and 3 is a biopsy channel or instrument channel, which serves to guide forceps or other instruments into a body cavity, along with a nozzle 5 which spurts out a cleaning liquid or compressed air to clean the observation window 3.

Figure 2:
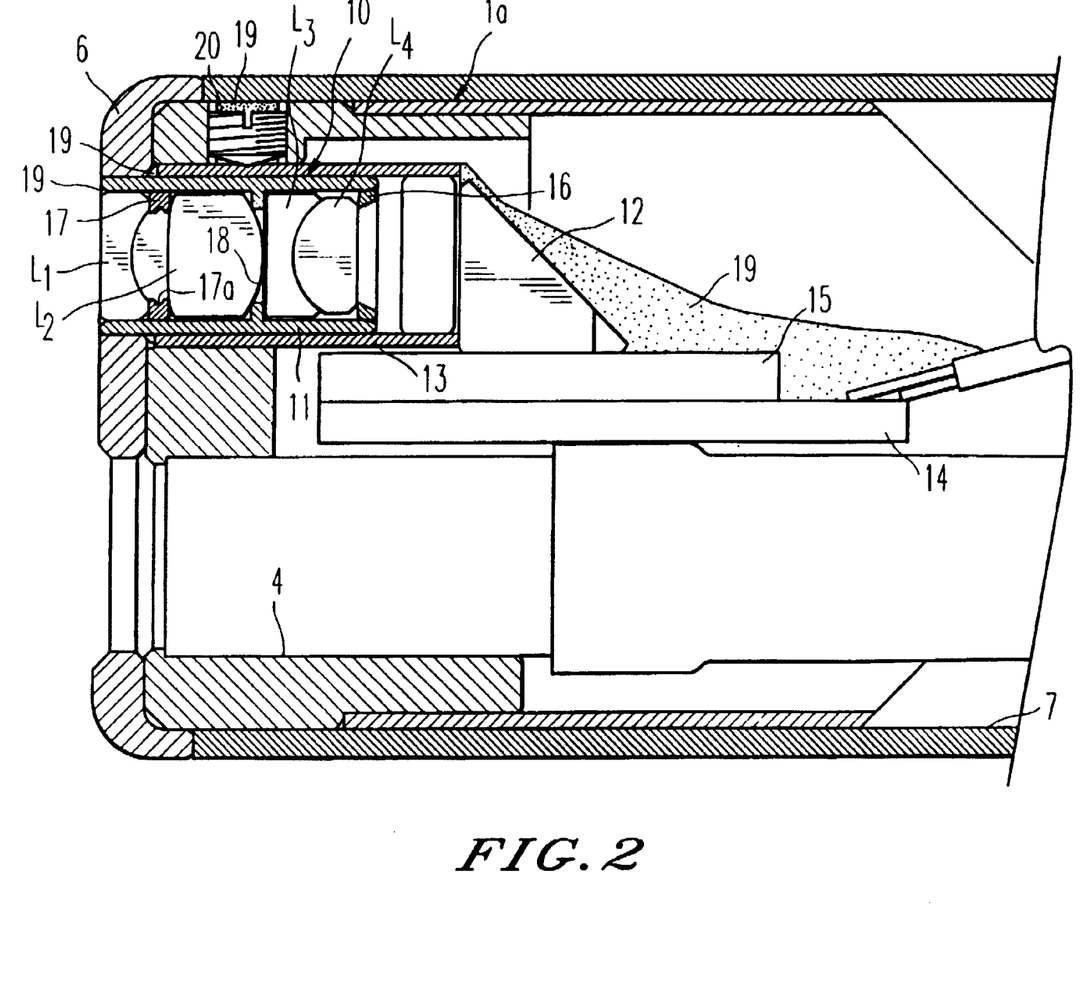
FIG. 2 is a schematic sectional view on an enlarged scale of a tip end section of the endoscopic insertion rod.

Shown on an enlarged scale in FIG. 2 is the tip end section 1a of the endoscopic insertion rod 1 which is provided with a plural number of axial bores for mounting the illumination system and the optical image pickup system and for an instrument channel or channels 4 etc. Normally, the tip end section 1a which contains a plural number of bores is formed of metal or other rigid material for the purpose of guaranteeing necessary structural strength and for improving machining accuracy in forming a number of axial bores required. Fitted on the distal end of the tip end section 1a is an end cap 6 of synthetic resin material which is provided with apertures in axial alignment with the illumination window 2, observation window 3, instrument channel 4 and nozzle 5. An outer skin layer 7 of the main flexible rod section is extended across the angle section 1b and joined with the end cap 6 in such a manner as to enshroud the entire insertion rod 1 in an electrically insulated state. This arrangement prevents any metal part of the insertion rod from being exposed directly on the outer side, protecting patients against electrical shocks which could otherwise occur, for example, when a high-frequency bioptic instrument is inserted in the instrument channel 4.

An objective lens unit 10 is mounted within a bore which is formed in the tip end section 1a of the insertion rod 1 contiguously with the observation window 3. The objective lens unit 10 is composed of a plural number of lens elements which are mounted in a lens barrel 11. Fitted on the inner end of the lens barrel 11 is a holder frame 13 of a prism 12 which is located behind the lens barrel 11 to turn the light path at right angles toward a solid-state image sensor 15. The solid-state image sensor 15 is mounted on a substrate 14 and cemented to the prism 12. If desired, the solid-state image sensor may be directly connected to the lens barrel 11 without using a prism.

For instance, the objective lens unit may be of a construction which is composed of four lens elements $L_1$ to $L_4$ as shown in FIG. 2. In this case, the first lens element $L_1$ which is in the foremost position is a plano-convex lens having a flat surface on the front side or on the side of the subject and a concave surface on the image-forming side. The second lens element $L_2$ which is located next to the first lens element $L_1$ is a plano-convex lens having a convex surface on the image-forming side. Further, the second and third lens elements $L_3$ and $L_4$ are constituted by a cemented lens. The first and second lens elements $L_1$ and $L_2$ are axially spaced apart from each other by a gap of a predetermined width, while the second lens element $L_2$ is partly abutted on the third lens element $L_3$. A stopper ring 16 is provided at the inner end of the lens barrel 11 on the image-forming side of the fourth lens element $L_4$, and a spacer ring 17 is fitted between the first and second lens elements $L_1$ and $L_2$. Further, an annular spacer rib 18 is provided on the inner periphery of the lens barrel 11 at a position between the second and third lens elements $L_2$ and $L_3$.

For the purpose of hermetically closing the lens barrel 11, the first lens element L1 in the foremost position is securely bonded to the lens barrel 11 by the use of an adhesive. In addition, in order to enhance the hermetic tightness of the lens barrel 11, the fore distal end of the barrel 11 is tightly fitted in the end cap 6. Seal material 19 is filled in an annular groove of V-shape in section, which is formed between outer marginal edge portions of the first lens element $L_1$ and inner peripheral edges at the outer end of the lens barrel 11. Further, seal material 19 is also applied to cover the prism frame 13, prism 12 and solid-state image sensor 15. The prism frame 13 which is assembled with the lens barrel 11 is fixedly mounted in a predetermined position on the tip end section 1a of the endoscopic insertion rod 1 by means of a set screw 20, which is covered with seal material 19.

The spacer ring 17 between the first and second lens elements $L_1$ and $L_2$ is formed of a material of high thermal conductivity like metal. Similarly, the lens barrel 11 is formed of a metal or other material with high thermal conductivity. On the other hand, the prism frame 13 which is fitted on the lens barrel 11 is formed of an electrically insulating material like synthetic resin. As a result, the lens barrel 11 is maintained electrically out of contact with other conducting parts like the tip end section 1a of the insertion rod 1 to preclude possibilities of current leakage which might otherwise occur during use of a high-frequency bioptic instrument.

When the endoscopic insertion rod 1 is introduced into a body cavity of a patient, the tip end section 1a tends to pick up temperature under the influence of body temperature of the patient or due to heat generation by the solid-state image sensor 15, up to a temperature level equivalent with or higher than the patient's body temperature, while it is being retained in the body cavity over a relatively long period of time. On the other hand, a washing liquid to be spurted onto the observation window 3 from the nozzle 5 is held in a tank which is normally not equipped with a heater. Therefore, the first lens $L_1$ is cooled down as soon as the washing liquid is spurted from the nozzle 5 to clean the observation window 3. On such an occasion, the supply of washing liquid would not give rise to any problem in particular as long as air in the space between the first and second lens elements $L_1$ and $L_2$ is dry air which is completely free of moisture. However, if it contains moisture even in a slight amount, fogging or moisture condensation will occur as a result of temperature drops of the first lens $L_1$.

Nevertheless, while the first lens $L_1$ is undergoing temperature drops to a certain degree by contact with the cold washing liquid which is spurted out from the nozzle 5, the cold washing liquid also comes into contact with the lens barrel 11 which is formed of a metal with far higher thermal conductivity as compared with the first lens $L_1$ and which is in abutting engagement with the spacer ring 17 of a metal of high thermal conductivity. Therefore, when the washing liquid is spurted out from the nozzle 5 toward the observation window 3, the lens barrel 11 and spacer ring 17 are cooled down more quickly than center portions of the first lens element $L_1$, and should moisture exist in the air gap between the first and second lens elements L1 and L2, it tends to condense firstly on those surfaces which are at lower temperatures. That is to say, moisture tends to condense on the spacer ring 17 which is the quickest one to be cooled by the washing liquid.

Figure 3:
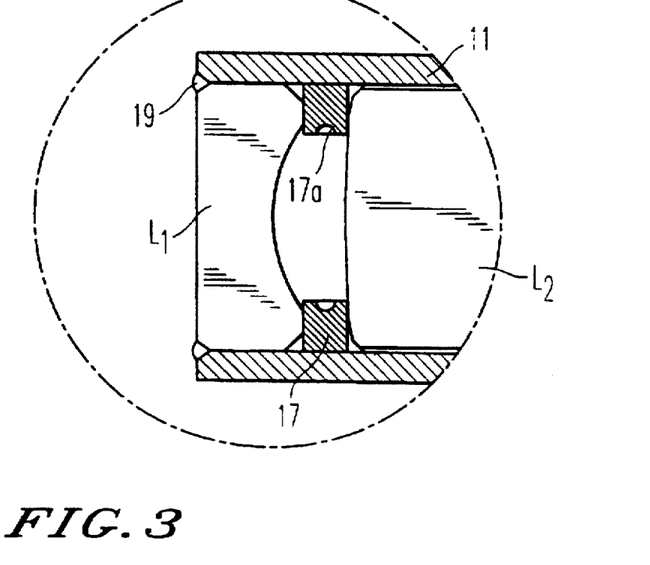
FIG. 3 is a fragmentary sectional view of a lens device in one embodiment of the present invention.

However, the spacer ring 17, which is relatively small in thickness, does not have enough room on its surfaces for deposition of a large amount of moisture. Therefore, it is desirable to shape the spacer ring 17 in such a manner as to increase its surface area as much as possible. For example, as shown in FIG. 3, the inner periphery of the spacer ring 17 may be formed in an arcuately concave shape, providing an arcuate moisture deposition surface 17a with a broadened surface area which permits a greater amount of moisture deposition. Since the air space between the first and second lens elements $L_1$ and $L_2$ is initially filled with moisture-free dry air and shielded by the seal material 19, the moisture content in the air space, if any, should be of such a small amount which can be totally taken up by the moisture depositing surface 17a of the spacer ring 17, leaving the first lens $L_1$ completely free of moisture deposition or suppressing moisture deposition on the first lens element substantially to such an amount which would not cause fogging to endoscopic observation images.

A temperature difference across the lens barrel 11 occurs not only at the time of washing the observation window 3 as described above, for example, but also when using an endoscope after high-temperature sterilization in which the endoscope as a whole is treated with a high temperature. In any case, fogging of the first lens element $L_1$ can be prevented by the preferential moisture deposition on the moisture depositing surface 17a of the spacer ring 17.

Figure 4:
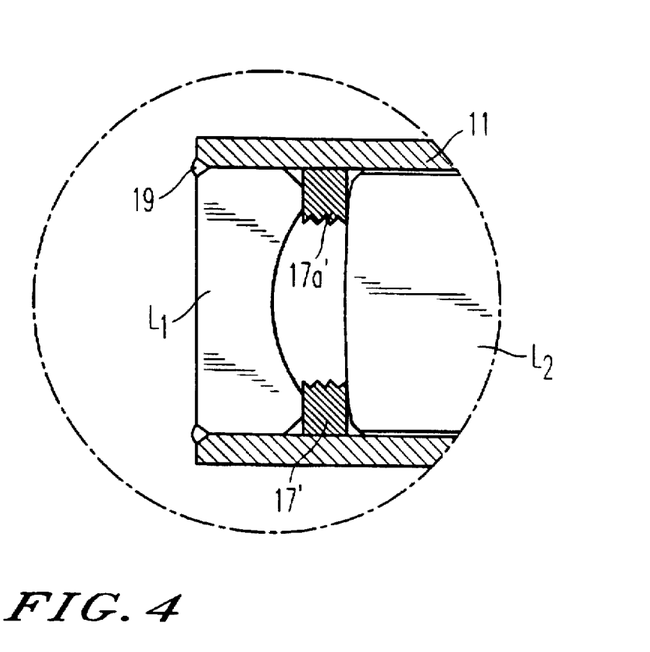
FIG. 4 is a fragmentary sectional view of a lens device in another embodiment of the present invention.

There may be employed a spacer ring 17 of a shape other than the one which is shown in FIG. 3, for instance, there may be employed a spacer ring 17' which is provided with tapped grooves on a moisture depositing surface 17a' on its inner periphery as shown in FIG. 4. In this case, thanks to the tapped grooves, the moisture depositing surface 17a' of the spacer ring 17' has a greater surface area for moisture deposition, and, in addition to the function of preventing the fogging of the first lens element $L_1$, contributes to further improve the quality of endoscopic observation images picked up by the solid-state image sensor 15, scattering harmful components of incident light rays by irregular reflections on the tapped grooves.

In this manner, the objective lens unit of the invention prevents fogging of the surfaces of the first lens element $L_1$ by preferentially condensing moisture in the air gap between the first and second lens elements $L_1$ and $L_2$, if any. However, in case an unexpectedly large amount of moisture exists in the air gap, the spacer ring 17 might fail to maintain sufficient anti-fogging effects on the first lens element $L_1$. In order to avoid such a situation, it is important for the lens barrel 11 to be hermetically tight enough for preventing intrusion of moisture from outside. This is the reason why the seal material 19 is packed between the lens barrel 11 and the first lens element $L_1$. For improving the hermetical tightness of the lens barrel 11, it is desirable to make adjustments as described below.

Firstly, it is necessary to check for errors as occurring in the process of assembling the respective lens elements into the lens barrel, as well as deviations from the focus position of the objective lens unit 10 as occurring when connecting the prism 14 and solid-state image sensor 16 to the prism frame 13. In order to locate the solid-state image sensor 15 exactly at the focus of the objective lens unit 10, the distance between the objective lens 10 and the image sensor 15 is adjusted by moving the lens barrel 11 in the direction of the optical axis. More particularly, the final adjustment of the focus position is normally made by shifting the position of the lens barrel 11 axially in the forward and backward directions about ±0.2 mm from a reference position adopted in an assembling stage, namely, axially over a distance of about 4 mm in total. For this purpose, the lens barrel 11 is fitted in the prism frame 13 loosely to permit the axial sliding movements in that range, and therefore, it is necessary to hermetically seal all gap spaces or clearances when fixing the lens barrel 11 to the prism frame 13 subsequent to the final adjustments, because otherwise the lens barrel 11 will easily lose air-tightness. After assembling together the lens barrel 11 relative to the prism frame 13 and making adjustments of the focus position as described above, seal material 19 is filled in the clearances at the fore end of the prism frame 13 as shown in FIG. 2 to seal up all open gaps. However, the seal material which can be applied to fill in the small gaps is limited in amount and therefore it is difficult to maintain a sufficient seal strength by the seal material 19 alone, which may suffer from degradations in seal strength as a result of impregnation of moisture.

Figure 5:
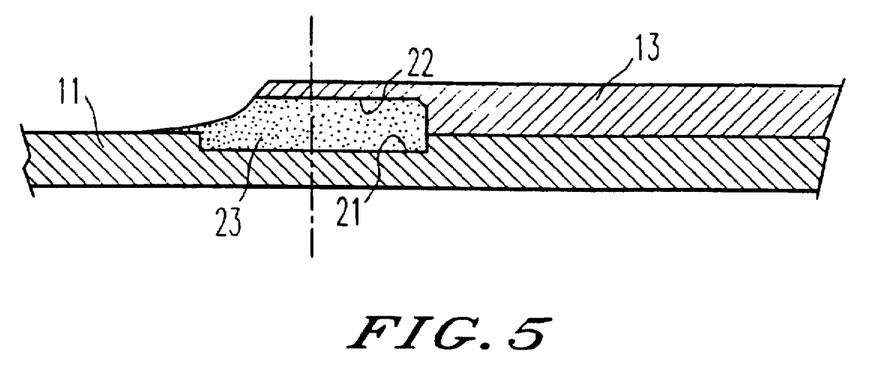
FIG. 5 is a fragmentary sectional view of a seal pocket packed with a seal material to hermetically shield the clearances between lens barrel and prism frame.

In order to seal the open gaps or clearances between the lens barrel 11 and the prism frame 13 more perfectly, it is desirable to provide a seal pocket between these members, including an annular groove 21 formed on and around the outer periphery of the lens barrel 11 in face to face relation with a stepped sunken wall portion 22 formed on the inner periphery of a fore end portion of the prism frame 13 as shown particularly in FIG. 5. Preferably, this seal pocket is packed with an adhesive type seal material 23. Considering that the adjustment of focus position can be made by varying the relative positions of the lens barrel 11 and prism frame 13 within an extremely fine range of ±0.2 mm axially in the forward or backward direction from the reference position P indicated in the same figure, the seal pocket which is constituted by the annular groove 21 on the lens barrel 11 and the annular sunken wall portion 22 on the prism frame 13 should have a width greater than the axial focus position adjustment range. By arranging a seal pocket in this manner, it can always be formed between the lens barrel 11 and the prism frame 13 although its shape might be changed in a slight degree when the lens barrel 11 is axially displaced relative to the prism frame 13 for the adjustment of focus position. The annular groove 21 is preferred to be as deep as possible within a range which would not impair the strength of the lens barrel 11.

The provision of the seal pocket of this nature makes it possible to pack a greater amount of seal material 23 in the narrow gap space between the lens barrel 11 and the prism frame 13 to form a seal of greater strength which can ensure hermetical tightness of the objective lens in a securer manner. The seal pocket can keep moisture out of the lens barrel 1 even when outer part of the seal material 23 is moistened to some extent due to deposition or impregnation of water. Besides, as the seal material 23 hardens into a solid state within the seal pocket, it is strongly bonded to stepped wall portions of the annular groove 21 of the lens barrel 11 as well as to stepped portions of the sunken wall portion 22 of the prism frame 13 to form an anchor seal. Thanks to the anchoring effects of the seal material 22, the lens barrel 11 and prism frame 13 are stably retained in the adjusted positional relations, precluding deviations of the lens barrel 11 from the adjusted focus position.

Figure 6:
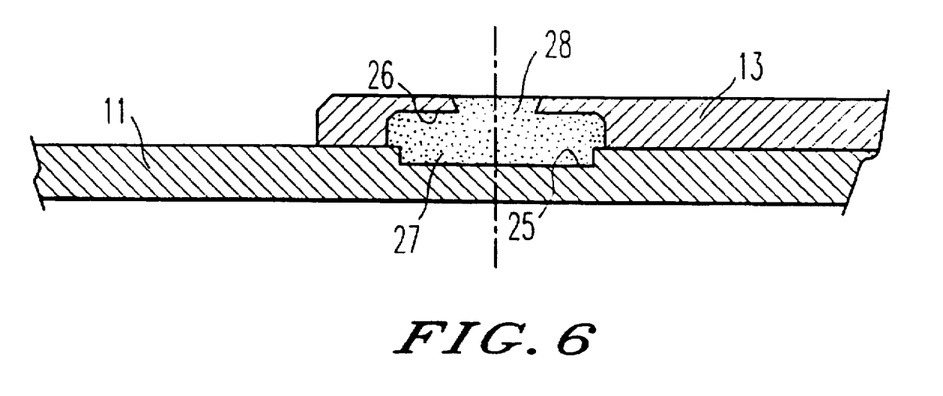
FIG. 6 is a fragmentary sectional view of a seal pocket of modified construction similarly packed with a seal material to hermetically shield the clearances between lens barrel and prism frame.

If desired, the seal pocket may be arranged in a form other than the above-described from, for example, in the form as shown in FIG. 6. In this case, a seal pocket is formed by an annular groove 25 which is provided on the outer periphery of the lens barrel, substantially in the same dimensions as the annular groove 21 of FIG. 5, and an annular groove 26 which is provided on the inner periphery of the prism frame 13 face to face with the annular groove 25. These annular grooves 25 and 26 are formed in such positions that centers of the two grooves are aligned in the radial direction when the lens barrel 11 is located in a predetermined reference position relative to the prism frame 13. The widths in the axial direction of the annular grooves 25 and 26 are determined on the basis of the range in which the lens barrel 11 is to be moved for adjustments of the focus position as described hereinbefore. In this regard, the two grooves 25 and 26 may be formed in the same width in the axial direction, or alternatively the groove 26 on the prism frame 13 may be formed in a larger width than the groove 25 on the lens barrel 11. Seal material 27 is packed in the pocket which is defined between the two grooves 25 and 26. To this end, the prism frame 13 is provided with a seal material charging hole 28 in communication with the groove 26. Thus, the seal pocket of this construction can also provide a stronger hermetical seal for the space between the lens barrel 11 and prism frame 13.

Figure 7:
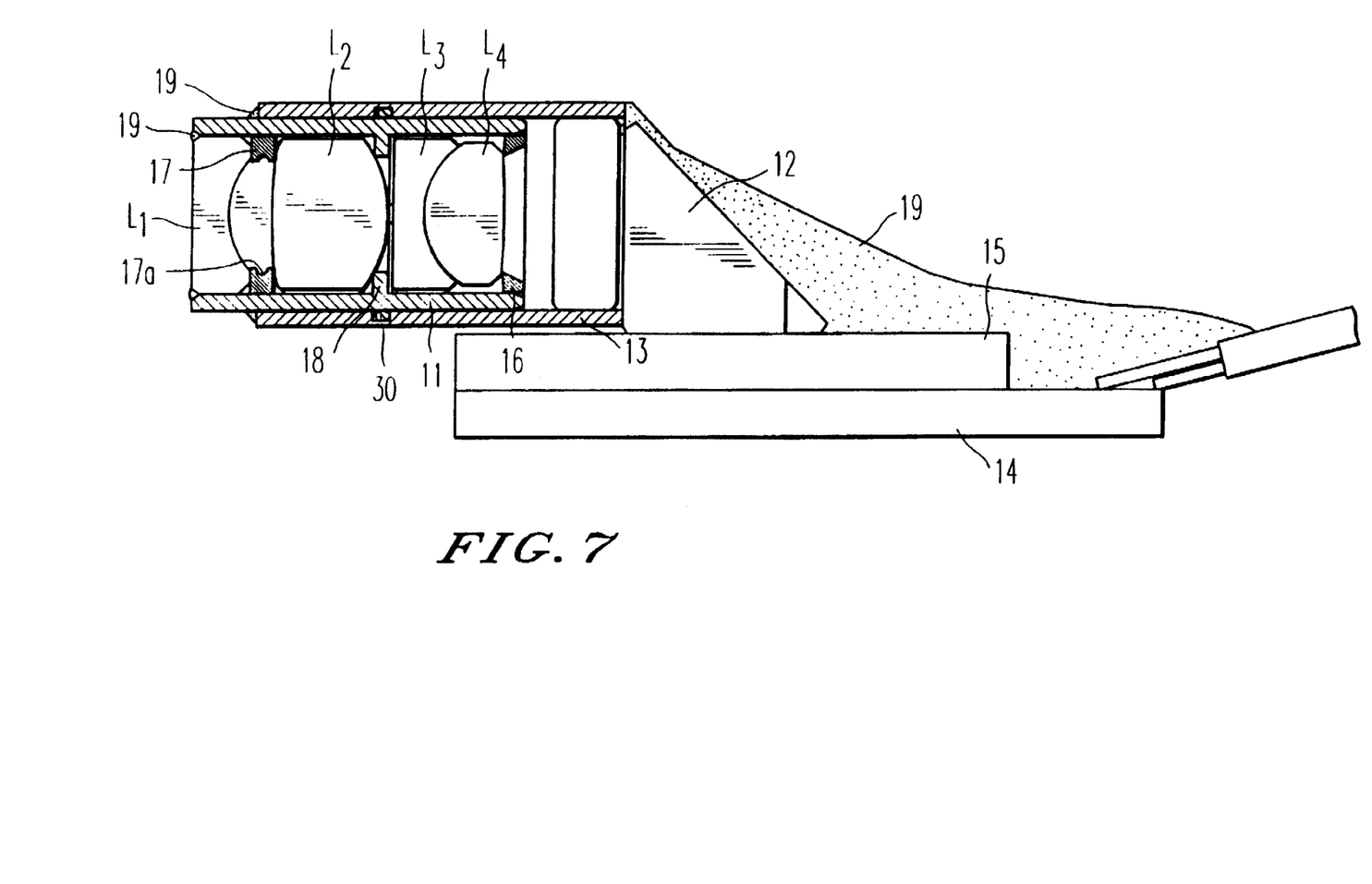
FIG. 7 is a sectional view of a lens device having a seal member interposed between lens barrel and prism frame.
Figure 8:
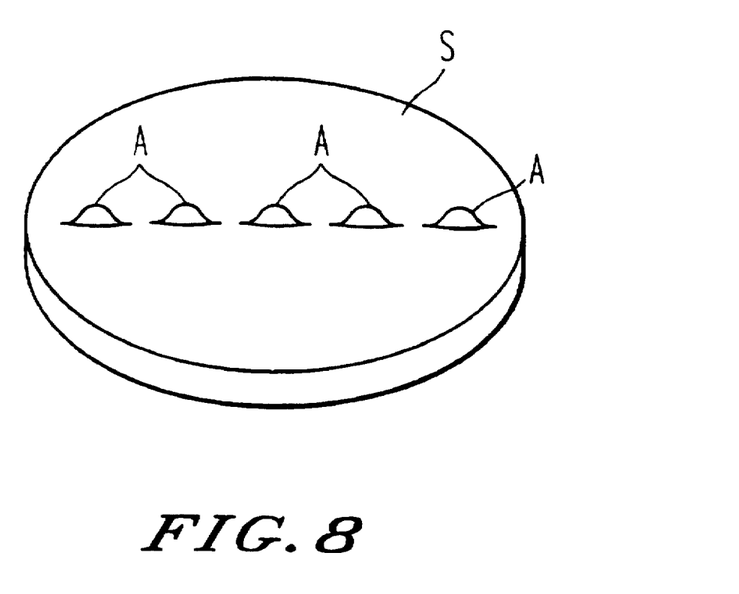
FIG. 8 is a schematic perspective view of an adhesive deposited on a glass surface.
Figure 9:
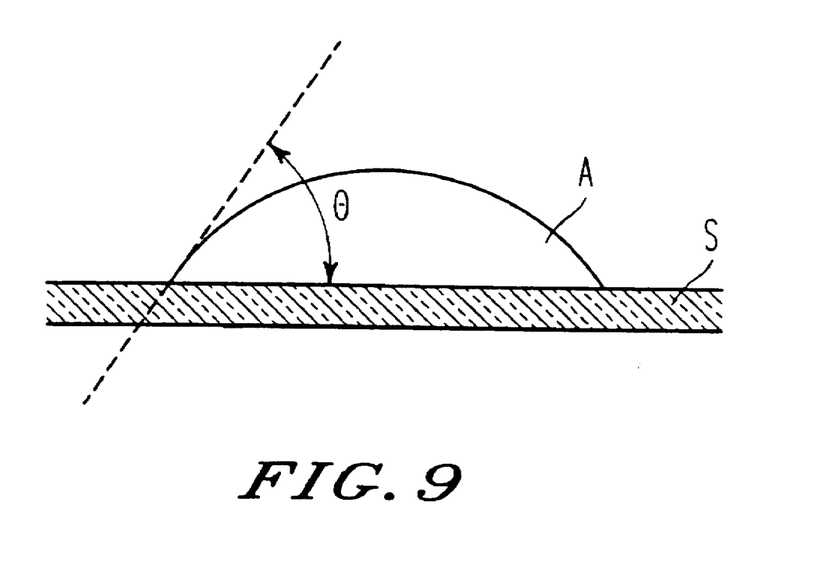
FIG. 9 is a schematic illustration explanatory of a wetting angle of an adhesive on the glass surface.

Further, a hermetical seal may be formed by interposing a seal member like an O-ring 30 between the lens barrel 11 and prism frame 13 as shown in FIG. 7. In this case, the seal member 30 is accommodated in an annular groove 31 which is formed on the inner periphery of the prism frame 13 with an increased thickness.

While the gap space between the lens barrel 11 and prism frame 13 can be sealed perfectly by the arrangements as described above, the hermetical seal between the first lens element $L_1$ and lens barrel 11 can be improved further by using a suitable adhesive as described below.

The adhesive to be used for bonding the first lens element $L_1$ to the lens barrel 11 should have suitable compatibility with both metal and glass. Generally epoxy resin adhesives are employed for filling clearances between metal and glass materials. As for solvent, it is preferable to use an alcoholic solvent, for example, acetone or the like. Among others, solvents such as cyclopentanone, n-pentanol, n-hexanol are preferred. Alternatively, benzene, methylene carbide, o-cyclolbenzene or butylnitrile can be used.

Figure 10:
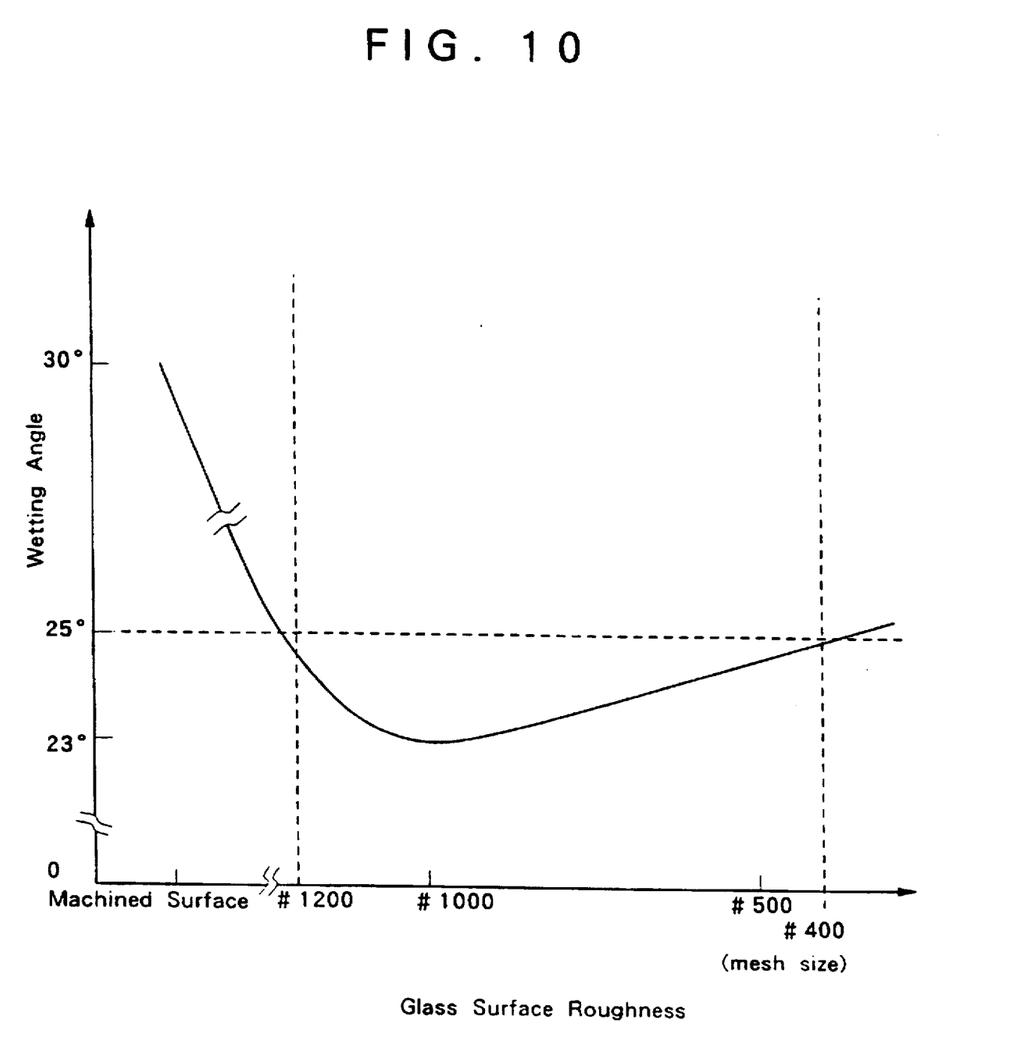
FIG. 10 is a diagram showing relations between wetting angle and strength of adhesion.

In selecting an adhesive, it is important to consider the wettability, a factor which has great influences on the adhesion or adhesive strength. More specifically, the wettability indicates the extent to which an adhesive agent can spread and wet the surfaces to be bonded. The higher the wettability, the greater becomes the adhesive strength. Namely, use of an adhesive with high wettability is extremely advantageous in forming strong hermetical tightness between bonded components. Generally, wettability of a bonding surface by an adhesive is expressed by way of a wetting angle. More particularly, an adhesive is dropped on a surface of bonding material S to measure a rising angle of a semi-globular mound of the adhesive as a wetting angle indicative of its wettability. From the standpoint of securing higher adhesion and hermetical tightness, the adhesive agent should have a smaller wetting angle on the first lens element $L_1$. Of course, the wettability of an adhesive agent varies not only in relation with the properties of the adhesive and of the material to be bonded, but also depending upon the surface conditions of the bonding material. In this regard, it has been generally accepted that a bonding surface should be made as smooth as possible to better the wettability. However, this cannot be applied to wettability on glass as seen in the diagram of FIG. 10 which shows the relations between wetting angle θ of an adhesive on glass and strength of adhesion.

As clear from that diagram, the wetting angle becomes the smallest at a glass surface roughness of about #1,000 in mesh size. Accordingly, sufficient adhesion strength can be obtained at #400 to #1,200 in mesh size, and, at these small wetting angles, the adhesive can be spread in an accelerated manner to ensure sufficient air tightness at the bonded joint.

Figure 11:
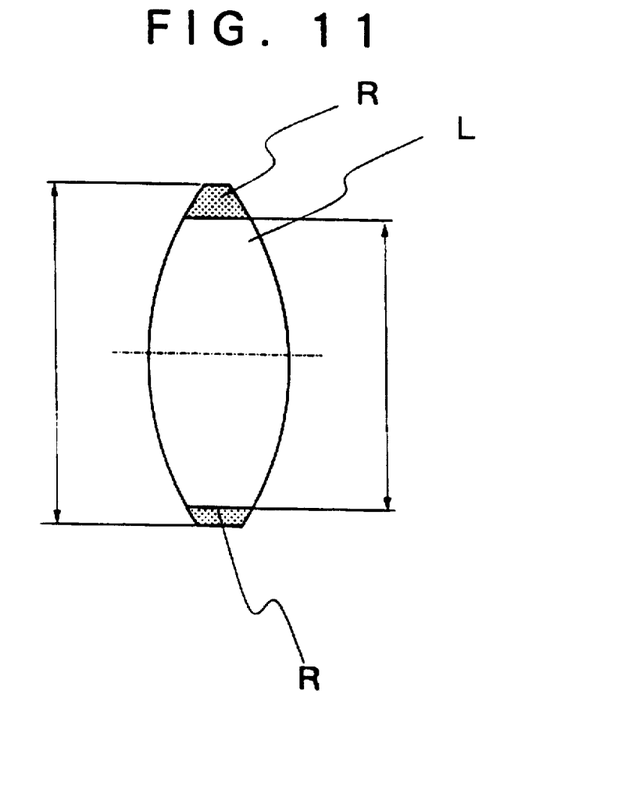
FIG. 11 is a schematic view of a lens element having machined surfaces in outer peripheral portions thereof.

It follows that adhesion strength as well as hermetical tightness can be improved by controlling the glass surfaces to a predetermined roughness. More specifically, it is preferred to machine peripheral surfaces of the first lens element L1 to a mesh size of #400 to #1,200, more preferably, to a mesh size of approximately #1,000. As seen in FIG. 11, preferably the lens element is formed in a slightly larger size in diameter in a manufacturing stage, and afterwards reduced to a predetermined diameter by a grinding operation, removing extra marginal portions R (indicated by hatching in the same figure) which are provided for centering purposes.

Figure 12:
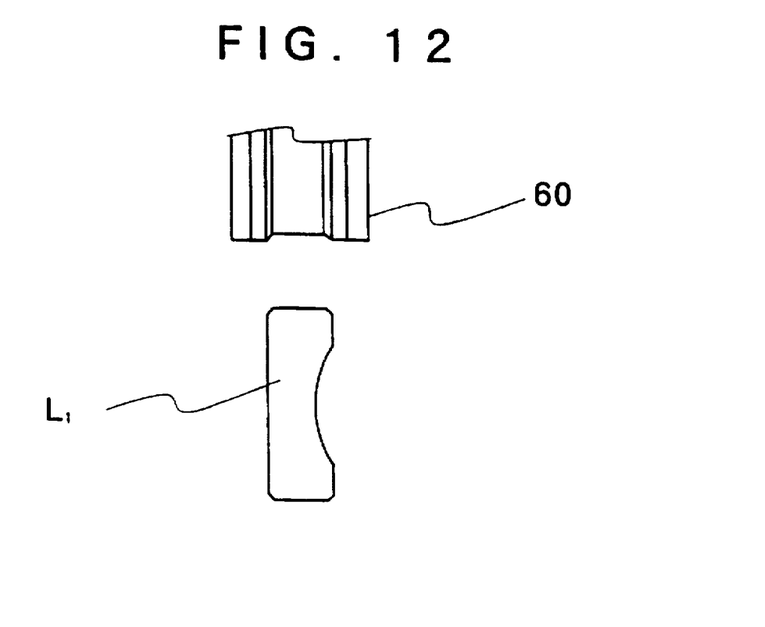
FIG. 12 is a schematic view of a grinding stone adopted for machining the lens elements.

In removing outer peripheral portions of the lens element by a grinding operation, for example, there may be employed a grinding stone as shown at 60 in FIG. 12. In abrading outer peripheral portions of the first lens element $L_1$ by a grinding operation, it is important to control the surface roughness to a mesh size of approximately #1,000 as mentioned above. By so doing, an applied epoxy resin adhesive can be spread uniformly over the entire machined surfaces of the first lens element $L_1$ and strongly bonded with the latter at the time of mounting the lens element in the lens barrel 11. Consequently, the first lens element $L_1$ can be securely bonded and fixed to the lens barrel 11 by the adhesive which is uniformly spread between the lens element $L_1$ and the lens barrel 11 entirely around the respective outer and inner peripheries, making it possible to maintain an extremely high hermetical seal over a long period of time.

As clear from the foregoing description, the lens device according to the present invention is completely shielded with strong hermetical seal means at the gap spaces or clearances between the lens barrel 11 and prism frame 13 as well as at the clearances between the lens barrel 11 and first lens element L1, so that, once dry air is charged into the lens barrel 11, it can preclude the fogging phenomenon due to existence of moisture in the gap space between the first and second lens elements $L_1$ and $L_2$. Even if moisture creeps into the gap space during use over a long period of time, the lens device still retains extremely high anti-fogging functions since such moisture is preferentially condensed on moisture depositing surfaces of the spacer ring 17. Therefore, when used on an endoscopic insrtion rod or under circumstances where a large temperature difference occurs between the inner and outer sides of the lens barrel, it can always prevent fogging of the first lens element L1 or other optical elements of the lens device especially in the passage areas of image-forming light rays.

What is claimed is:

1. A lens device having a plural number of optical lens elements mounted within a cylindrical lens barrel, including a first lens element located in a foremost position on the side of a subject and a second lens element located behind and at a space from said first lens element, said lens device comprising:

a spacer ring fitted in said lens barrel to set apart said first and second lens elements by a gap space of a predetermined width, said spacer ring being formed of a material having higher thermal conductivity than said lens elements and, on the side of inner periphery thereof, provided with a moisture depositing surface formed in a non-flat shape to increase surface area on said inner periphery.

2. A lens device as defined in claim 1, wherein said lens barrel is formed of a metallic material of high thermal conductivity and mounted on an optical imaging system with a front end portion of said lens barrel in an exposed state.

3. A lens device as defined in claim 1, wherein said moisture depositing surface of said spacer ring is formed in an arcuately concave shape in cross section in axial direction.

4. A lens device as defined in claim 1, wherein said moisture depositing surface on the inner periphery of said spacer ring is formed with a large number of tapped grooves.

5. A lens device as defined in claim 1, wherein said lens barrel is incorporated into an endoscopic imaging system on a tip end portion of an endoscopic insertion rod, with a front end portion of said lens barrel in an exposed state.

6. A lens device as defined in claim 5, wherein said lens barrel is fitted in a cylindrical member axially slidably within a predetermined focus position adjustment range, and provided with an annular groove on and around the outer periphery thereof in association with a stepped sunken wall portion formed on and around the inner periphery of said cylindrical member to provide a seal pocket to be packed with a seal material.

7. A lens device as defined in claim 6, wherein said cylindrical member is provided with a stepped sunken wall portion on the inner periphery thereof over a predetermined length from a fore distal end thereof, said annular groove on said lens barrel being located in such a position as to come into radially overlapping relation with said annular groove on said lens barrel when the latter is in said focus position adjustment range.

8. A lens device as defined in claim 6, wherein said lens barrel and cylindrical member are formed with annular groove on outer and inner peripheries thereof in radially overlapping relation with each other to provide said seal pocket, said annular grooves on said lens barrel and cylindrical member each having an axial length greater than a slidable range of said lens barrel corresponding to said focus position adjustment range, and said cylindrical member is provided with a seal material supply port opened on the outer periphery thereof in communication with said annular groove.

9. A lens device as defined in claim 6, wherein said lens barrel is axially slidably fitted in said cylindrical member for adjustments of focus position of an objective lens member and hermetically shielded by a seal material filled in clearances between said lens barrel and said cylindrical member.

10. A lens device as defined in claim 1, wherein said first lens element is bonded to said lens barrel by the use of an adhesive, outer peripheral surfaces of said first lens element being machined to a predetermined roughness to improve wettability of said adhesive.

11. A lens device as defined in claim 10, wherein said adhesive is an epoxy resin adhesive.

12. A lens device as defined in claim 10, wherein the outer peripheral surfaces of said first lens element are machined to a roughness of #400 to #1,200 in mesh size.

* * * * *